United States Patent [19]

Frey

[11] Patent Number: 4,687,488
[45] Date of Patent: Aug. 18, 1987

[54] FEMUR HEAD PROSTHESIS

[75] Inventor: Otto Frey, Winterthur, Switzerland

[73] Assignee: Silver Brothers Limited, Winterthur, Switzerland

[21] Appl. No.: 649,492

[22] Filed: Sep. 11, 1984

[30] Foreign Application Priority Data

Nov. 15, 1983 [CH] Switzerland ............ 6127/83

[51] Int. Cl.$^4$ .............................................. A61F 2/36
[52] U.S. Cl. .................................................. 623/22
[58] Field of Search ................ 3/1.9, 1.91, 1.911, 3/1.912, 1.913; 128/92 C, 92 CA

[56] References Cited

U.S. PATENT DOCUMENTS 3,064,645 11/1962 Ficat et al. ............... 128/92 CA
4,032,994 7/1977 Frey ............................ 3/1.912
4,058,856 11/1977 Doerre et al. ............. 128/92 CA
4,528,702 7/1985 Frey ........................... 128/92 CA

FOREIGN PATENT DOCUMENTS 2289160 7/1976 France ......................... 3/1.912

Primary Examiner—Richard J. Apley
Assistant Examiner—David J. Isabella
Attorney, Agent, or Firm—Francis C. Hand

[57] ABSTRACT

The femur head prosthesis is constructed with a sleeve for mounting on the pin of an anchoring shank. The sleeve is provided with a slotted end which is of smaller diameter than the end of the pin so as to plastically deform about the pin when mounted therein. The plastic deformation permits a clamped connection which prevents rotation of the femur head prosthesis on the anchoring shank.

11 Claims, 4 Drawing Figures

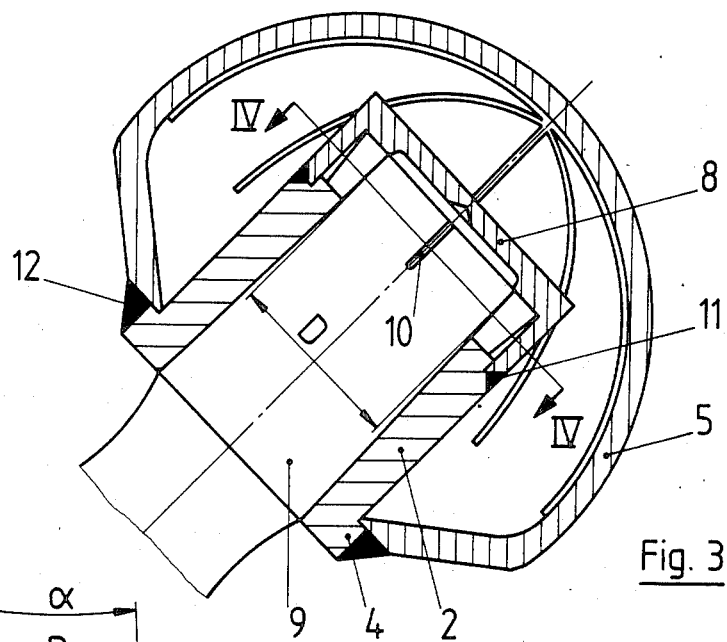
Fig. 3
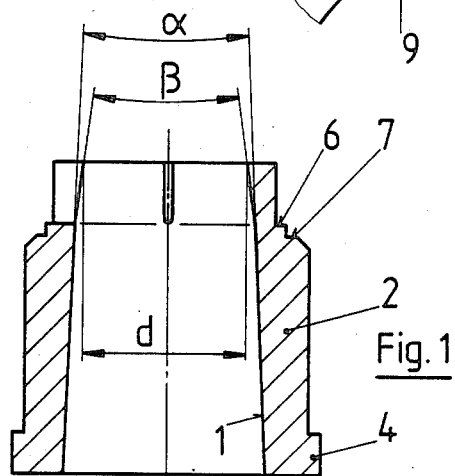
Fig. 1
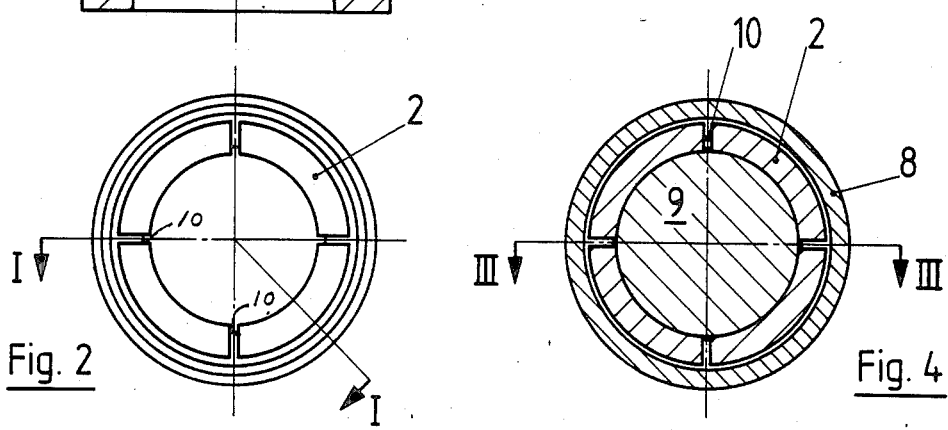
Fig. 2
Fig. 4

FEMUR HEAD PROSTHESIS

This invention relates to a femur head prosthesis.

As is known ball joint endoprostheses, particularly a femur head prosthesis have frequently been constructed of a joint head and an anchoring shank which are connected to each other. One measure which is frequently used for connecting the joint head to the anchoring shank consists of a cone plug connection wherein the joint head is plugged onto a pin of the anchoring shank, for example through a self-locking cone as described in German OS No. 2548077. However, in the case of relatively large joint heads which are subjected to increased torsion moments, as used, for example in the so-called fracture prosthesis, undesired relative rotations often occur after implantation between the joint head and the pin.

It has also been known from Swiss Pat. No. 507,704 and German PS No. 2220304 how to attach a joint head on a pin through a conical plug connection in which the pin axis does not coincide with the axis of symmetry of the joint head so as to be able to approximate the position of the joint head relative to the femur axis depending upon the individual differences in the skeletal structure of various patients. For such prostheses with an "oblique" position of the two axes, the joint head must not rotate relative to the pin during the life of the prostheses. To this end, the base of the pin has been provided with various types of anti-rotation devices. For example, the base of the pin has been provided with ribs, noses, teeth, or the like which are adapted to engage in corresponding radial grooves in a conical female surface within the joint head. However, quite apart from the fact that the making of the grooves in the conical female surface requires a rather high expense, such an anti-rotation device has the disadvantage that a stepless (continuous) adjustment of the joint head relative to the pin is not permitted. Instead, this type of anti-rotation device only permits a relative rotation and fixation of the joint head relative to the pin which corresponds to the number of grooves.

Accordingly, it is an object of the invention to provide a femur head prosthesis which can be fastened onto a pin of an anchoring shank without regard to a specific angular position between the prosthesis and the pin.

It is another object of the invention to be able to fixedly position a joint head of a femur head prosthesis on an anchoring shank in any one of a universal number of positions.

It is another object of the invention to mount a joint head of a femur head prosthesis on an anchoring shank in a non-rotatable manner.

It is another object of the invention to reduce the time required by a surgeon to implant a femur head prosthesis.

Briefly, the invention provides a femur head prosthesis which is comprised of a shell-shaped joint head and a sleeve which is secured to and disposed within the joint head. In accordance with the invention, the sleeve has a first tapered internal conical surface extending from an outer end towards a second end within the joint head as well as a second tapered internal conical surface extending from the first surface to that second end. Further, the second conical surface has a cone angle greater than the cone angle of the first conical surface.

When in use, the femur head prosthesis is placed on an anchoring shank which has a tapered pin at one end. In this regard, the femur head prosthesis is fitted over the tapered pin so that the first tapered surface is matingly received about the pin while the second tapered surface is plastically deformed around the end of the pin.

As the pin of the anchoring shank is positioned and driven or pressed into the sleeve of the femur head prosthesis, the tapered end of the sleeve expands and effects a clamped connection with a relatively large holding area between the surfaces of the pin and sleeve. Expansion of the sleeve can be facilitated by providing a plurality of circumferentially spaced radial slots within the tapered surface at the inner end of the sleeve.

In order to preclude any possibility of body fluid penetrating into the shell-shaped joint head, along the clamped surfaces of the pin and femur head prosthesis, a cover is provided at the end of the sleeve to cover the slots and to close the end of the sleeve. In this regard, the cover is sized so as to cover over the radial slots in the manner of a hood.

The femur head prosthesis is formed primarily of metal, for example any metal and/or alloy which has been known for use in an endoprosthesis.

These and other objects and advantages of the invention will become more apparent from the following detailed description taken in conjunction with the accompanying drawings wherein:

FIG. 1 illustrates a cross-sectional view taken on line I—I of FIG. of a sleeve of a femur head prosthesis in accordance with the invention;

FIG. 2 illustrates an end view of the sleeve illustrated in FIG. 1;

FIG. 3 illustrates a view taken on line III—III of FIG. 4 of a femur head prosthesis constructed in accordance with the invention; and FIG. 4 illustrates a view taken on line IV—IV of FIG. 3.

Referring to FIG. 3, the femur head prosthesis is comprised of a shell-shaped joint head 5 and a sleeve 2 which is secured to and disposed within the joint head 5.

Referring to FIG. 1, the sleeve 2 has a first tapered internal conical surface 1 which extends from one end of the sleeve towards a second end, i.e. the upper end as viewed. The sleeve 2 also has a shoulder 4 about the lower end, as viewed, for supporting the joint head 5 as indicated in FIG. 3. The upper end of the sleeve 2 is also provided with external shoulders 6, 7 which are stepped so as to receive a cover 8 as shown in FIG. 3.

Referring to FIG. 3, the joint head 5 is secured to the base 4 of the sleeve 2 by means of a weld 12. In like manner, the cover 8 is secured to the sleeve 2 by means of a circumferential weld 11.

As indicated in FIG. 1, the upper end of the sleeve 2 is spaced from the joint head 5 and is provided with a second tapered internal conical surface which extends from the first conical surface 1 to the upper end of the sleeve 2. Further, this second surface has a cone angle $\beta$ greater than the cone angle $\alpha$ of the first conical surface 1.

Referring to FIGS. 1, 2 and 3, the upper end of the sleeve 2 is provided with a plurality of circumferentially spaced radial slots 10, for example four slots. These slots 10 extend through the second conical tapered surface of the sleeve 2.

Referring to FIG. 3, the femur head prosthesis is mounted on a tapered pin 9 of an anchoring shank for a femur prosthesis. In this regard, the pin 9 has a conical angle which is matched to the conical angle α of the conical surface 1 of the sleeve 2. When the femur head prosthesis is mounted in place, the conical surface 1 of the sleeve 2 is matingly received on the pin 9 while the second tapered conical surface which contains the slots 10 is plastically deformed against the end of the pin 9. In this regard, by way of example, the sleeve has an inside diameter d at the end which is less than the diameter D of the pin 9 at the end thereof. For example, the inside diameter of the sleeve 2 is 14 millimeters while the diameter at the end of the pin is 14.2 millimeters with a tolerance of 1-2/100 millimeters.

As a comparison of FIGS. 2 and 4 illustrate, the slots 10 and the sleeve 2 widen circumferentially when the sleeve 2 has been completely mounted on the pin 9. Further, as indicated in FIG. 3, the cover 8 is disposed over the end of the sleeve 2 with a radial gap therebetween. However, when the pin 9 is completely mounted within the sleeve 2, this gap is reduced in size.

Of note, during assembly, the cover 8 is first placed over the end of the sleeve 2 after cutting of the slots 10. After being welded in place, the cover 8 serves to close off the end of the sleeve 2 in fluid tight relationship. Thereafter, the joint head 5 is placed on and connected with the sleeve 2 via the weld seam 12.

In use, when the pin 9 of the anchoring shank is inserted into the sleeve 2 of the femur head prosthesis, there is an initial radial clearance due to the end of the pin 9 being of slightly small diameter than the internal diameter at the entrance end of the sleeve 2. As the pin 9 passes into the sleeve 2, the conical surface 1 of the sleeve 2 and the conical surface of the pin 9 are brought into mating relation. However, as the pin 9 continues to move into the sleeve 2, the slotted end portion of the sleeve 2 begins to circumferentially expand. This causes a plastic deformation of the slotted end portion of the sleeve 2 to such an extent that a clamped connection is provided between the pin 9 and sleeve with a relatively large holding surface between the two parts. With the axes of the pin 9 and sleeve 2 coincident, there is no need for a surgeon to be concerned with the position of the pin 9 relative to the sleeve 2. With an "oblique" position of the two axes the clamp connection provides for a stepless adjustment of the joint head relative to the pin. Further, the clamp connection provides a positive anti-rotation effect so as to prevent undesired relative rotations between the joint head and pin after implantation.

The invention thus provides a femur head prosthesis which can be readily used by a surgeon and can be manipulated onto the pin of an anchoring shank in a universal matter.

What is claimed is:

1. A femur head prosthesis for mounting on a pin of an anchoring shank comprising
   a shell-shaped joint head, and
   a sleeve secured to and disposed within said joint head, said sleeve having a first tapered internal conical surface extending from an open end towards a closed second end within said joint head, a second tapered internal conical surface extending from said first surface to said closed end, said second surface having a cone angle greater than the cone angle of said first surface and a plurality of radial slots formed in said second surface distributed circumferentially of said sleeve, whereby when said femur head prosthesis is mounted in place, said sleeve is matingly received on the pin and said second tapered conical surface plastically deforms relative to the pin thereby non-rotatably securing said femur head prosthesis to anchoring shank.

2. A femur head prosthesis as set forth in claim 1 which further comprises a cover at said second end of said sleeve covering said slots and closing said second end of said sleeve.

3. A femur head prosthesis as set forth in claim 1 wherein said sleeve is welded to said joint head at said open end.

4. A femur head prosthesis as set forth in claim 1 wherein said sleeve and joint head are made of metal.

5. In combination,
   an anchoring shank for a femur prosthesis having a tapered pin at one end; and
   a femur head prosthesis mounted on said pin, said prosthesis having a shell-shaped joint head and a sleeve secured to and within said joint head, said sleeve having a first tapered conical surface matingly received on said pin and a second tapered conical surface at a closed end plastically deformed against an end of said pin and spaced inwardly from said joint head to non-rotatably secure said femur head prosthesis to said anchoring shank wherein said sleeve is initially formed with said second conical surface on a greater cone angle than said first conical surface to permit plastic deformation of said second surface.

6. The combination as set forth in claim 5 wherein said sleeve includes a plurality of circumferentially spaced radial slots at said end of said sleeve.

7. The combination as set forth in claim 6 wherein said femur head prosthesis includes a cover at said end of said sleeve to cover said slots with a radial gap therebetween and close said end of said sleeve.

8. The combination as set forth in claim 5 wherein said sleeve has an inside diameter at said end thereof less than a diameter of said pin at said end thereof.

9. The combination as set forth in claim 5 wherein said end has a plurality of circumferentially disposed slots therein and said femur head prosthesis includes a cover mounted on said sleeve to close said end of said sleeve, said cover being radially spaced about said end.

10. A femur head prosthesis for mounting a pin of an anchoring shank comprising
    a shell shaped joint head; and
    a sleeve secured at an open end to said joint head and extending into said joint head to a closed second end, said sleeve having a first tapered internal conical surface extending from said open end towards said closed end and a second tapered internal conical surface extending from said first surface to said closed end, said second surface having a cone angle greater than the cone angle of said first surface and being circumferentially expandable, whereby when said femur head prosthesis is mounted in place, said sleeve is matingly received on the pin and said second tapered conical surface plastically deforms relative to the pin thereby non-rotatably securing said femur head prosthesis to the anchoring shank.

11. A femur head prosthesis as set forth in claim 10 wherein said second surface is slotted.

* * * * *

UNITED STATES PATENT AND TRADEMARK OFFICE
CERTIFICATE OF CORRECTION

PATENT NO. : 4,687,488

DATED : August 18, 1987

INVENTOR(S) : OTTO FREY

It is certified that error appears in the above-identified patent and that said Letters Patent is hereby corrected as shown below:

Column 2, line 29 "Fig." should be "Fig. 2"
Column 3, line 29 "small" should be -smaller-
Column 3, line 52 "matter" should be -manner Signed and Sealed this Twenty-ninth Day of March, 1988

Attest:

DONALD J. QUIGG

*Attesting Officer*  *Commissioner of Patents and Trademarks*